United States Patent
Nakajima

(10) Patent No.: US 9,429,567 B2
(45) Date of Patent: Aug. 30, 2016

(54) METHOD FOR SCREENING SUBSTANCES HAVING WEIGHT-REGULATING ACTION

(76) Inventor: Toshihiro Nakajima, Kanagawa (JP)

(*) Notice: Subject to any disclaimer, the term of this patent is extended or adjusted under 35 U.S.C. 154(b) by 41 days.

(21) Appl. No.: 14/127,422

(22) PCT Filed: Jun. 22, 2012

(86) PCT No.: PCT/JP2012/065944
§ 371 (c)(1),
(2), (4) Date: Dec. 18, 2013

(87) PCT Pub. No.: WO2012/176860
PCT Pub. Date: Dec. 27, 2012

(65) Prior Publication Data
US 2014/0127705 A1 May 8, 2014

(30) Foreign Application Priority Data
Jun. 22, 2011 (JP) .................. 2011-138145

(51) Int. Cl.
*C12Q 1/68* (2006.01)
*G01N 33/50* (2006.01)

(52) U.S. Cl.
CPC ......... *G01N 33/5044* (2013.01); *C12Q 1/6883* (2013.01); *G01N 33/5008* (2013.01); *C12Q 2600/136* (2013.01); *G01N 2333/9015* (2013.01)

(58) Field of Classification Search
CPC ............... G01N 33/5044; G01N 33/5008; C12Q 1/6683; C12Q 2600/136
See application file for complete search history.

(56) References Cited

U.S. PATENT DOCUMENTS
2004/0152871 A1   8/2004   Nakajima et al.

FOREIGN PATENT DOCUMENTS
WO   WO 02/52007     4/2002
WO   WO 2010/024852  3/2010

OTHER PUBLICATIONS

Tsuchimochi et al., identification of a crucial site for Synoviolin Expression, Molecular and Cellular Biology, Aug. 2005, p. 7344-7356.*
Nakajima, Toshihiro: "Experimental Medicine", vol. 25 (3), pp. 418-421, 2007.
International Search Report mailed on Jul. 31, 2012 in International Patent Application No. PCT/JP2012/065944.
Tetsuya, Amano et al.: "Synoviolin/Hrd1, and E3 Ubiquitin Ligase, as a Novel Pathogenic Factor for Arthropathy", Genes and Development, vol. 17(19), Oct. 1, 2003, pp. 2436-2449.
Extended European Search Report mailed on Jan. 20, 2015 in European Patent Application No. 12802212.6.

* cited by examiner

*Primary Examiner* — Reza Ghafoorian
(74) *Attorney, Agent, or Firm* — Fanelli Haag PLLC

(57) ABSTRACT
The present invention relates to a method for screening substances having weight-regulating action.

2 Claims, 4 Drawing Sheets

FIG 5
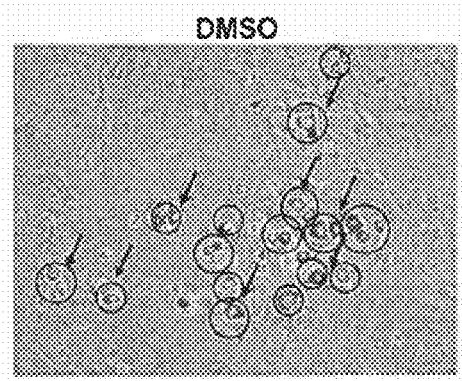
DMSO
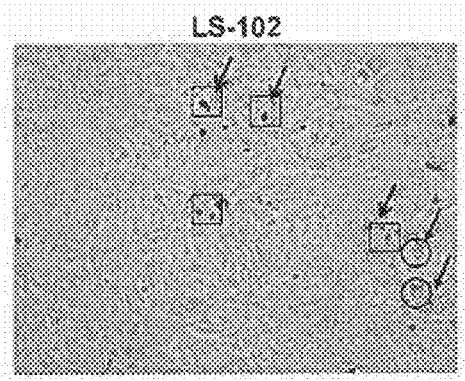
LS-102
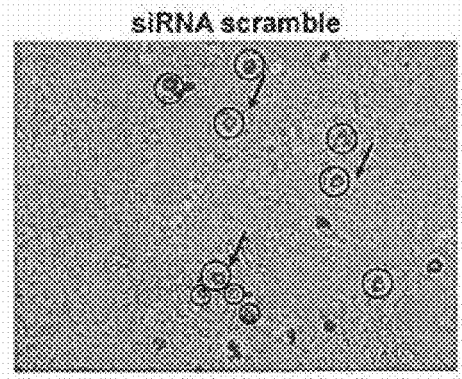
siRNA scramble
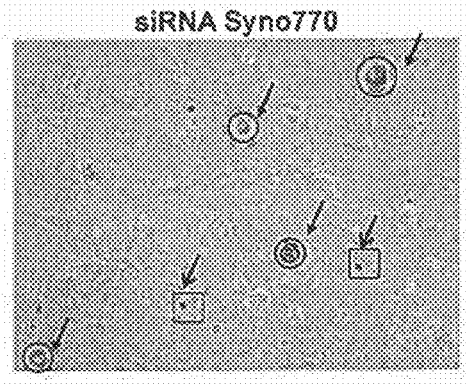
siRNA Syno770

METHOD FOR SCREENING SUBSTANCES HAVING WEIGHT-REGULATING ACTION

TECHNICAL FIELD

The present invention relates to a method for screening substances having weight-regulating action.

BACKGROUND ART

Synoviolin is a protein which was discovered as a membrane protein that is over-expressed in synovial cells obtained from rheumatoid arthritis patients (Patent Document 1). Synoviolin has been determined to be a molecule that is essential for the onset of rheumatoid arthritis according to research conducted using genetically modified animals.

Synoviolin has been suggested to have a RING finger motif based on analyses using a protein structure prediction system. This motif is found in large numbers in an enzyme known as E3 ubiquitin ligase, which plays an important role in protein ubiquitination. In actuality, synoviolin has been demonstrated to have self-ubiquitination activity, which is a characteristic of E3 ubiquitin ligase (Patent Document 1). However, many of the functions of synoviolin in vivo remain unknown. More specifically, there have been no reports regarding whether the disruption of synoviolin gene causes weight loss.

Obesity is caused by such factors as lack of exercise, habitual overeating or metabolic disorders attributable to genetic factors or endocrine diseases. Obesity is a risk factor that can induce various adult-onset diseases such as myocardial infarction or arteriosclerosis, and since it also contributes to exacerbation of these diseases, early treatment and prevention are extremely important. Although treatment involving hormone drugs or metabolism promoting agents has conventionally been used in pharmacotherapy for obesity, hardly any drugs are known that are able to reduce weight safely or inhibit weight gain.

PRIOR ART DOCUMENTS

Patent Documents

[Patent Document 1] International Publication No. WO 02/052007

DISCLOSURE OF THE INVENTION

Problems to be Solved by the Invention

With the foregoing in view, the development of a substance is sought that has weight-regulating action.

Means for Solving the Problems

The inventor of the present invention found for the first time that disruption of synoviolin gene causes weight loss using synoviolin gene conditional knockout mice, thereby leading to completion of the present invention.

Namely, the present invention is as indicated below.

[1] A method for screening substances having weight-regulating action, comprising: contacting a test substance with synoviolin gene-expressing cells, and identifying whether or not the test substance has an effect on expression of synoviolin gene.

[2] The method described in [1], wherein the effect on expression of synoviolin gene is inhibition of expression of synoviolin gene or inactivation of expressed protein thereof.

[3] The method described in [1], wherein the effect on expression of synoviolin gene is promotion of expression of synoviolin gene or activation of expressed protein thereof.

[4] A pharmaceutical composition for regulating body weight, comprising: a nucleic acid consisting of a contiguous base sequence of 20 to 25 bases complementary to a transcription product of synoviolin gene, wherein the nucleic acid suppresses expression of synoviolin gene.

[5] A pharmaceutical composition for regulating body weight, comprising: a ubiquitination activity inhibitor of synoviolin protein.

[6] A method for screening substances having adipose tissue quantity-regulating action, comprising: contacting a test substance with synoviolin gene-expressing cells, and identifying whether or not the test substance has an effect on expression of synoviolin gene.

[7] The method described in [6], wherein the effect on expression of synoviolin gene is inhibition of expression of synoviolin gene or inactivation of expressed protein thereof.

[8] The method described in [6], wherein the effect on expression of synoviolin gene is promotion of expression of synoviolin gene or activation of expressed protein thereof.

[9] A pharmaceutical composition for regulating the amount of adipose tissue, comprising: a nucleic acid consisting of a contiguous base sequence of 20 to 25 bases complementary to a transcription product of synoviolin gene, wherein the nucleic acid suppresses expression of synoviolin gene.

[10] A pharmaceutical composition for regulating the amount of adipose tissue, comprising: a ubiquitination activity inhibitor of synoviolin protein.

[11] A method for screening substances having adipocyte differentiation induction-regulating action, comprising: contacting a test substance with synoviolin gene-expressing cells, and identifying whether or not the test substance has an effect on expression of synoviolin gene.

[12] The method described in [11], wherein the effect on expression of synoviolin gene is inhibition of expression of synoviolin gene or inactivation of expressed protein thereof.

[13] The method described in [11], wherein the effect on expression of synoviolin gene is promotion of expression of synoviolin gene or activation of expressed protein thereof.

[14] A pharmaceutical composition for regulating induction of adipocyte differentiation, comprising: a nucleic acid consisting of a contiguous base sequence of 20 to 25 bases complementary to a transcription product of synoviolin gene, wherein the nucleic acid suppresses expression of synoviolin gene.

[15] A pharmaceutical composition for regulating induction of adipocyte differentiation, comprising: a ubiquitination activity inhibitor of synoviolin protein.

Effects of the Invention

According to the method of the present invention, a substance can be provided that has a novel weight-regulating action.

BRIEF DESCRIPTION OF THE DRAWINGS

FIG. 5 indicates the effects of suppression of synoviolin gene on induction of adipocyte differentiation in 3T3-L1 cell line. ○: Differentiated adipocytes, □: Fat droplets that are not normal adipocytes.

BEST MODE FOR CARRYING OUT THE INVENTION

Figure 1:
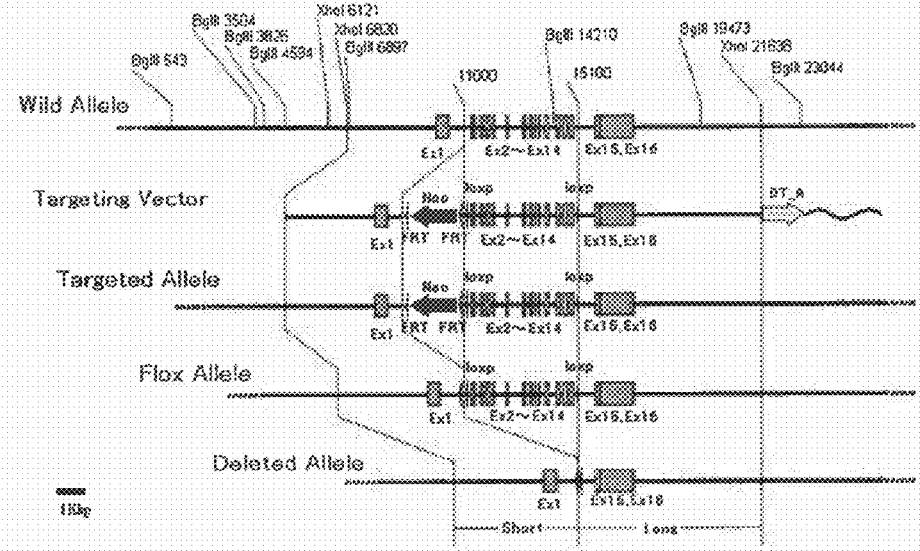
FIG. 1 is a design drawing of a gene targeting vector.

An arbitrary substance can be used for the test substance used in the present invention. There are no particular limitations on the type of test substance, and may be a low molecular weight synthetic substance, compound present in a natural product extract, or synthetic peptide. Alternatively, the test substance can be selected from a compound library, phage display library or combinatorial library.

In the present invention, weight-regulating action refers to an action that causes a change in body weight by a significant difference before and after treatment. Weight-regulating action acts through, for example, regulation of the amount of adipose tissue or regulation of the induction of adipocyte differentiation.

Synoviolin is an E3 ubiquitin ligase that functions in endoplasmic reticulum-associated degradation, and is universally present in mammals. In addition, the base sequence of synoviolin can be acquired from a known database. For example, the accession number of human synoviolin is AB024690.

Synoviolin gene knockout mice refer to mice in which the normal expression of synoviolin has been inhibited as a result of artificially modifying the sequence of the synoviolin gene region, and as a result thereof, preventing synoviolin from functioning normally in the body.

In addition, a portion or all of synoviolin gene can be modified or deleted. Here, "all" of synoviolin gene refers to a region extending from the 5' end of exon 1 to the 3' end of the final exon of synoviolin genomic DNA. In addition, a "portion" of synoviolin gene refers to a portion of this region of a length required for inhibition of normal expression of synoviolin gene. Moreover, "modified" refers to changing the base sequence of a target region of genomic DNA to another base sequence by substituting, deleting, inserting and/or translocating one or a plurality of nucleotides.

A knockout animal in which a portion or all of synoviolin gene has been modified or deleted can be produced according to a known method. For example, a knockout animal can be produced using a gene targeting method as described in the following examples. In this method, by substituting a region at least containing the start codon of exon 1 of synoviolin gene with another base sequence by homologous recombination, normal expression of synoviolin can be inhibited. In addition, knockout animals used in the screening method of the present invention include not only knockout animals produced according to this method, but also progeny thereof.

The animals targeted for use as knockout animals of the present invention are non-human animals, and there are no particular limitations thereon. Examples include mammals such as cows, pigs, sheep, goats, rabbits, dogs, cats, guinea pigs, hamsters, mice or rats. Rabbits, dogs, cats, guinea pigs, hamsters, mice or rats are preferable for use as experimental animals. In particular, rodents are more preferable, while mice and rats are particularly preferable when considering that a large number of inbred strains have been produced as well as in consideration of techniques such as culturing of fertilized eggs or in vitro fertilization.

A portion of synoviolin gene of a target animal is isolated in order to construct a targeting vector. For example, in the case of producing a knockout mouse, a mouse genomic DNA library is screened for synoviolin gene. A targeting vector for homologous recombination is then constructed using the resulting genomic DNA clone. The genomic DNA clone is not required to be the full length of the gene. All required is cloning of a region required to suppress expression of synoviolin by disrupting synoviolin gene. In addition, the targeting vector can also be produced by a known method, and for example, can be produced by using a commercially available plasmid as a backbone and suitably linking respective fragments consisting of the aforementioned genomic DNA clone, a positive selection marker, a negative selection marker and the like.

The targeting vector produced according to the aforementioned method is then introduced into cells having the ability to form an individual (totipotency), such as fertilized eggs, early embryos or embryonic stem cells (ES cells), by electroporation and the like, followed by selecting those cells in which the target homologous recombination has occurred. Screening is carried out by selecting cells using chemical agents according to a positive-negative selection method. Following selection, those cells in which the target homologous recombination has occurred are confirmed by southern blotting or PCR and the like. Finally, cells for which the desired homologous recombination has been confirmed are introduced into an 8-cell stage embryo or blastocyst harvested from the fallopian tube or uterus during pregnancy.

The aforementioned 8-cell stage embryo or blastocyst is transplanted into an allomother in accordance with ordinary methods. By crossing the germ-line chimeric animals (preferably males) born from the allomother with wild-type animals (preferable females) homologous for the wild-type JLP gene, a first generation (F1) can be obtained in the form of heterozygotes in which one of the JLP genes on a homologous chromosome has been disrupted by homologous recombination. Moreover, by crossing these heterozygotes, a second generation (F2) can be obtained in the form of homozygotes in which both JLP genes on homologous chromosomes have been disrupted, namely the JLP knockout animals of the present invention. Homozygotes are identified by severing a portion of the body (such as the tail), extracting DNA and determining genotype by southern blotting or PCR and the like.

Although the following provides a more detailed explanation of the present invention using the following examples, the present invention is not limited by these examples.

EXAMPLES

The design drawing of a gene targeting vector used to produce synoviolin knockout mice of the present example is shown in FIG. 1. In the drawing, the structures of a normal synoviolin gene (Wild allele), targeting vector for producing a synoviolin knockout mouse (Targeting vector), allele that has undergone homologous recombination (Targeted allele), allele containing a loxP sequence (Flox allele) and allele from which loxP-Exons 2 to 14-loxP has been deleted (Deleted allele) are respectively schematically shown starting at the top in that order.

A region upstream from exon 1 and downstream from exon 16 of mouse synoviolin gene in the form of a 14.8 kb gene region was used to construct the targeting vector. A Neo resistance gene interposed between FRT sequences was inserted between exon 1 and exon 2. In addition, loxP sequences were introduced upstream from exon 2 and downstream from exon 14.

The aforementioned targeting vector was introduced into ES cells. Clones having an allele in which the target homologous recombination has occurred were selected by confirming removal of the loxP-exon-loxP sequence by Cre treatment and removal of the FRT-neomycin-FRT sequence by FLP treatment using the lengths of the PCR products.

Chimeric mice were obtained by introducing the aforementioned ES cell clones that had undergone homologous recombination into mouse embryos as described in a known method (e.g., EMBO J 16:1850-1857). Moreover, these chimeric mice were crossed with wild-type C57BL/6 mice to acquire mice in which the neomycin sequence had been removed. In addition, since loxP sequences between exons and the long arm incorporated in the targeting vector have the possibility of being lost during homologous recombination, their presence was confirmed by PCR.

The resulting neomycin-removed mice were crossed with CAG-CreER mice to obtain CAG-CreERsyno$^{fl/fl}$ mice.

Tamoxifen was administered to the resulting CAG-CreERsyno$^{fl/fl}$ mice (20 mg/ml (corn oil) 5 mg/40 g of body weight, intraperitoneal administration, consecutive administration for 5 days on days 0 to 4) to induce removal of loxP-exon-loxP (CAG-CreER(+)syno$^{fl/fl}$). A C57BL/6J group (vehicle control, tamoxifen-administered) and CAG-CreER(−)syno$^{fl/fl}$ group (vehicle control, tamoxifen-administered) were provided as controls.

Figure 2:
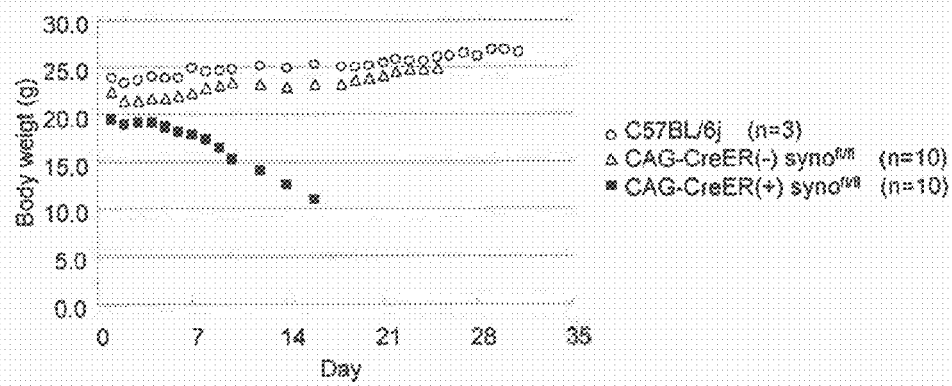
FIG. 2 indicates changes in body weight versus the number of rearing days.
Figure 3:
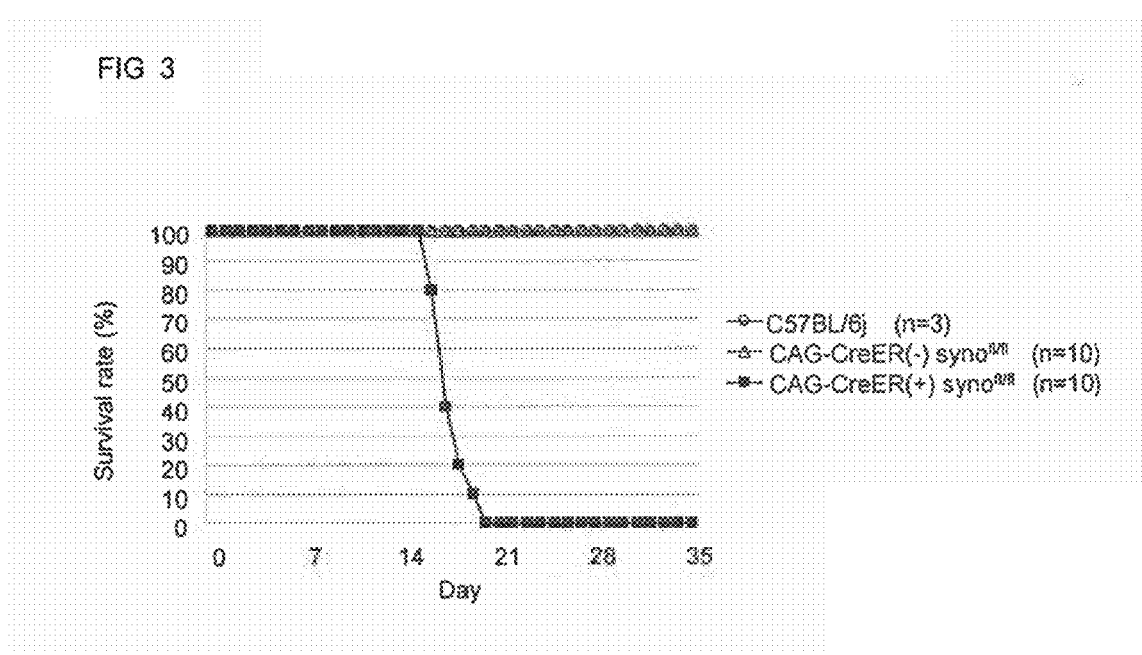
FIG. 3 indicates changes in survival rate versus the number of rearing days.

As a result, decreases in body weight dependent on the number of days the animals were housed were observed in the CAG-CreER(+)syno$^{fl/fl}$ tamoxifen-administered group. On the other hand, decreases in body weight were not observed in either of the control groups (FIG. 2). All of the animals of the CAG-CreER(+)syno$^{fl/fl}$ tamoxifen-administered group died on days 18 to 20 of rearing (FIG. 3). Autopsy of the dead animals revealed slight postmortem changes in organs of the abdominal and thoracic cavities. In addition, the spleen and gallbladder had decreased in size, and normally light yellow bile was colorless. There was extremely little subcutaneous, perirenal or peritesticular fat.

Mice tissue obtained after rearing for 16 days following administration of tamoxifen was fixed with 4% formaldehyde and embedded in paraffin followed by preparing adipose tissue sections with a microtome.

Figure 4:
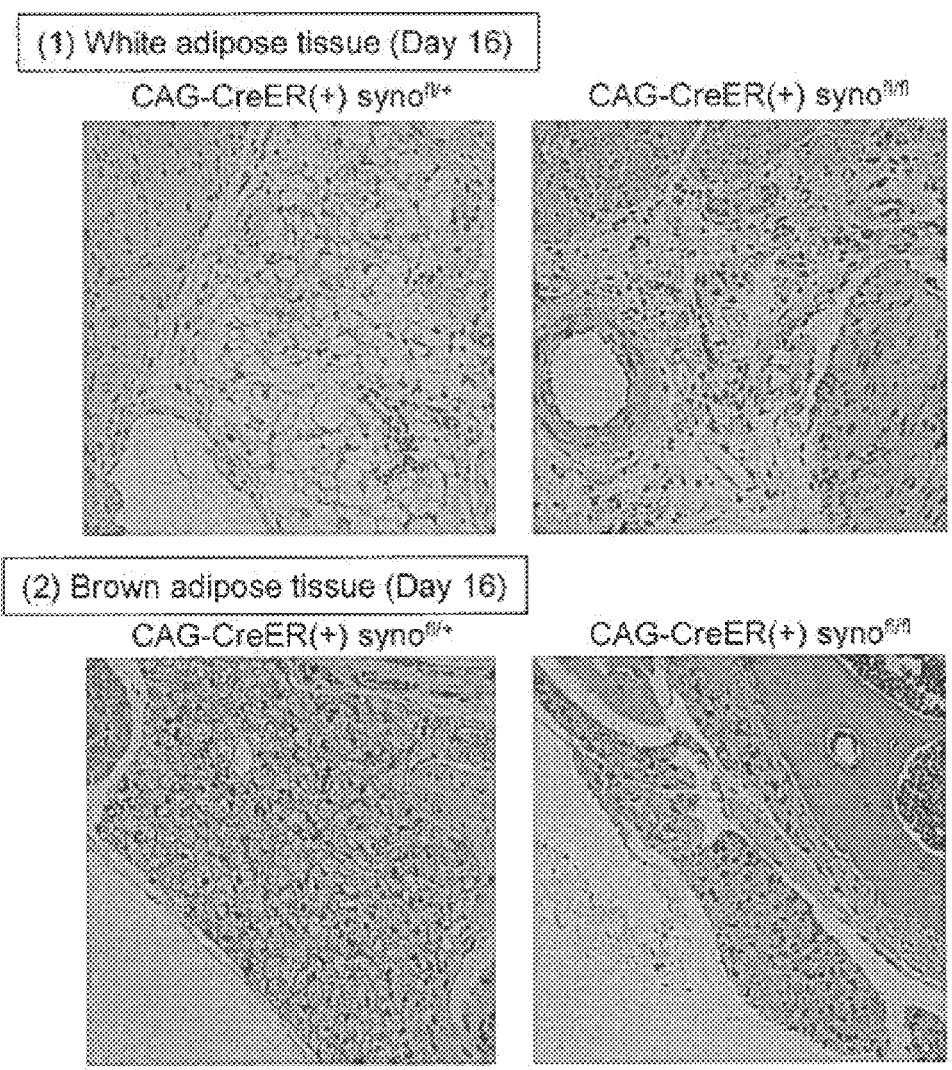
FIG. 4 depicts adipose tissue pathological sections obtained from synoviolin gene knockout mice and control mice on day 16 following administration of tamoxifen. (1) White adipose tissue, (2) Brown adipose tissue.

As a result, decreases in white adipose tissue and brown adipose tissue were observed in the synoviolin knockout mice (CAG-CreER(+)syno$^{fl/fl}$) in comparison with the synoviolin heterozygous knockout mice (CAG-CreER(+)syno$^{fl/+}$) (FIG. 4).

3T3-L1 cells were cultured for 3 days after reaching confluence in DMEM (10% FBS, High Glucose). Differentiation was induced by adding 500 μM IBMX, 1 μM dexamethasone and 5 μg/ml of insulin. 10 μM LS-102 (synoviolin ubiquitination activity inhibitor) or DMSO were added at the same time. After culturing for 3 days, the medium was replaced with medium containing 4 μg/ml of insulin followed by the addition of 10 μM LS-102 or DMSO. After again culturing for 3 days, the medium was replaced with DMEM (10% FES, High Glucose) followed by additionally culturing for 3 days. With respect to siRNA, 200 pmol of siRNA Syno770 was introduced using Lipofectamine 2000 two days prior to inducing differentiation.

Oil Red O Staining

After washing the 3T3-L1 cells with PBS(−), the cells were fixed with 10% formalin. The cells were then washed with PBS(−) and transferred to 60% isopropanol. The cells were stained for 20 minutes with 18 mg/ml of Oil Red O/Isopropanol and then washed with 60% isopropanol and PBS(−) followed by observing with a microscope.

As a result, in those cells in which synoviolin gene activity had been inhibited with LI102 or siRNA Syno770, the number of differentiated adipocytes was lower in comparison with the control, thereby suggesting that differentiation had been suppressed (FIG. 5). In addition, fat droplets were also observed that were not normal ring-like adipocytes.

INDUSTRIAL APPLICABILITY

The method of the present invention is useful for screening substances having weight-regulating action.

The invention claimed is:

1. A method for screening substances suppressing differentiation to an adipocyte comprising:
    contacting a test substance with synoviolin gene-expressing cells, identifying that the test substance inhibits expression of synoviolin gene or inactivates an expressed protein thereof, and identifying that the test substance suppresses differentiation to an adipocyte.

2. The method according to claim 1, wherein the effect on expression of synoviolin gene is inhibition of expression of synoviolin gene or activation of expressed protein thereof.

* * * * *